United States Patent [19]
Noda et al.

[11] 4,016,166
[45] Apr. 5, 1977

[54] 1-NITROPHENYLQUINAZOLINE-2,4(1H,3H)-DIONES

[75] Inventors: Kanji Noda, Chikushino; Akira Nakagawa, Tosu; Terumi Hachiya, Chiyoda; Hiroyuki Ide, Fukuoka, all of Japan

[73] Assignee: Hisamitsu Pharmaceutical Co., Inc., Japan

[22] Filed: Dec. 9, 1974

[21] Appl. No.: 531,097

[30] Foreign Application Priority Data

Dec. 14, 1973 Japan .................. 48-140556
Mar. 1, 1974 Japan ................... 49-24999
Mar. 28, 1974 Japan ................... 49-35325

[52] U.S. Cl. .................. 260/251 QA; 260/260; 424/251
[51] Int. Cl.² .............. C07D 239/95; C07D 239/96
[58] Field of Search ................ 260/25 QA, 260

[56] References Cited

UNITED STATES PATENTS 3,794,643   2/1974   Yabuuchi et al. .................. 260/260

FOREIGN PATENTS OR APPLICATIONS

| 2,100,623 | 1971   | France .................. 260/260 |
| 2,120,663 | 9/1975 | Germany ................ 260/260 |
| 705,742   | 1973   | Japan ................... 260/260 |
| 705,140   | 1975   | Japan ................... 260/260 |
| 546,243   | 1974   | Switzerland ............ 260/260 |
| 1,311,573 | 1973   | United Kingdom ......... 260/260 |
| 1,059,271 | 2/1967 | United Kingdom |
| 1,099,553 | 1/1968 | United Kingdom |

OTHER PUBLICATIONS

Coomas et al., J. Med. Chem., vol. 16, pp. 1237-1242 (1973).

*Primary Examiner*—Donald G. Daus
*Assistant Examiner*—Mary C. Vaughn
*Attorney, Agent, or Firm*—Browdy and Neimark

[57] ABSTRACT

The compounds of the present invention can be represented by the following formula:

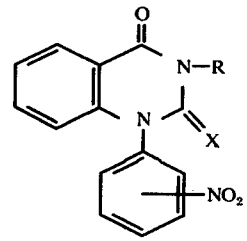

wherein R is selected from the group consisting of hydrogen, lower alkyl, unsaturated lower alkyl, substituted lower alkyl and aralkyl; X is selected from the group consisting of O and S, possessing a high degree of pharmacological activities such as anti-inflammatory, analgetic, and central nervous system depressive activities, and certain of them are useful as new anti-inflammatory agents, analgesics and central nervous system depressants.

14 Claims, No Drawings

1-NITROPHENYLQUINAZOLINE-2,4(1H,3H)-DIONES

DETAILED DESCRIPTION

The present invention relates to the compounds represented by the general formula I :

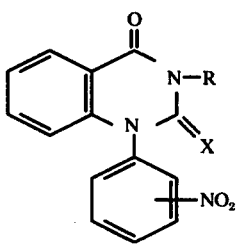

wherein R is selected from the group consisting of hydrogen, lower alkyl, lower alkenyl, lower alkynyl, aralkyl and lower alkyl substituted with a group selected from halogens, hydroxyl, alkanoyloxy, lower alkoxy, lower hydroxyalkoxy, lower cycloalkyl and lower alkoxycarbonyl ; X is selected from the group consisting of O and S.

The compounds of the present invention possess a high degree of pharmacological activities such as anti-inflammatory, analgetic, and central nervous system depressive activities as well as low toxicity, and certain of them are useful as new analgesics, anti-inflammatory agents and central nervous system depressants. All of the compounds of the present invention posses at least one of the said pharmacological activities, and most possess more than one of the said activities.

More particularly, the compounds of the present invention can be represented by the general formula I :

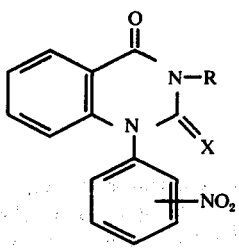

wherein R is selected from the group consisting of hydrogen, lower alkyl groups having from one to 6 carbon atoms, lower alkenyl groups having from 3 to 5 carbon atoms, propargyl, cyclopropylmethyl, haloethyl, trihaloethyl, acetoxyethyl, alkoxyalkyl groups having from 2 to 4 carbon atoms, lower hydroxyalkyl groups having from 2 to 3 carbon atoms, hydroxyethoxyethyl, ethoxycarbonylmethyl and benzyl ; X is selected from the group consisting of O and S.

The compounds of the present invention can be prepared in high yields by one of five independent processes which are illustrated by the following Reaction scheme I–V.

Preparation Series I

Reaction scheme [I]:

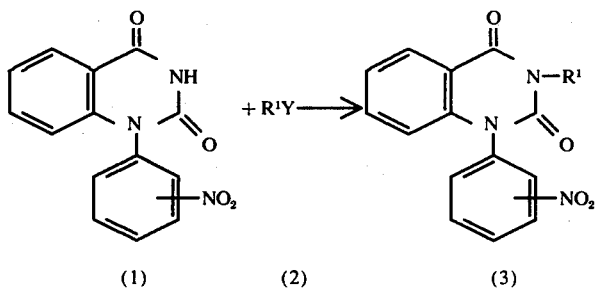

wherein $R^1$ is selected from the group consisting of lower alkyl, unsaturated lower alkyl, substituted lower alkyl and aralkyl ; Y is selected from the group consisting of halogen, organic sulfonyloxy, and organic and inorganic acid ester rest. Examples of compounds of the general formula (2) include methyl iodide, allyl bromide, 2,2,2 -trifluoroethyl p-toluenesulfonate, methyl fluorosulfate and trimethyl phosphate. The reaction represented by the reaction scheme [I] is preferably carried out in a suitable organic solvent such as dimethylformamide, tetrahydrofuran or benzene in the presence of a metallic compound such as sodium hydride, sodium amide or sodium alcoholate, an organic base such as pyridine or trialkylamine, or an inorganic base such as alkali hydroxide or alkali carbonate. The first-mentioned metallic compounds are most effective to obtain the highest yield of the object compounds. The reaction temperature is not critical. While the reactions proceed smoothly even at room temperature, they may be accelerated and finished in a short time by heating.

Reaction scheme [II] :

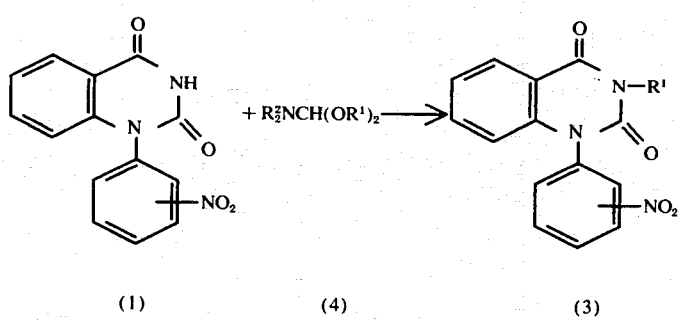

wherein $R^1$ has the same meanings as above ; $R^2$ is lower alkyl. Examples of compounds of the general formula (4) include N,N-dimethylformamide dimethyl acetal, N,N-dimethylformamide diisoprophl acetal and N,N-dimethylformamide ethyleneacetal. The reactions represented by the reaction scheme [II] are carried out at a temperature of 60 –160° C in a suitable organic solvent such as dimethylformamide, chloroform, benzene and tetrahydrofuran.

Preparation Series II

Reaction scheme [III] :

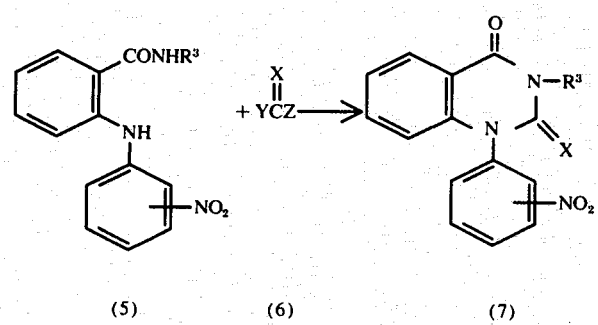

wherein $R^3$ is selected from the group consisting of hydrogen, lower alkyl, unsaturated lower alkyl, substituted lower alkyl and aralkyl ; Y is selected from the group consisting of halogen, alkoxy, organic sulfonyloxy and amino ; Z is selected from the group consisting of halogen, trihaloalkyl, alkoxy, aryloxy, alkoxcarbonyloxy and amino ; X is selected from the group consisting of O and S. Examples of compounds of the general formula (6) include urea, methylurea, diethylurea, N-propylurethane, 1,1′-carbonyldiimidazole, 1,1′-thiocarbonyldiimidazole, 1-ethoxycarbonylimidazole, phosgene, thiophosgene, ethyl chlorocarbonate, trichloroacetyl chloride and diethyl carbonate.

Reaction scheme [IV] :

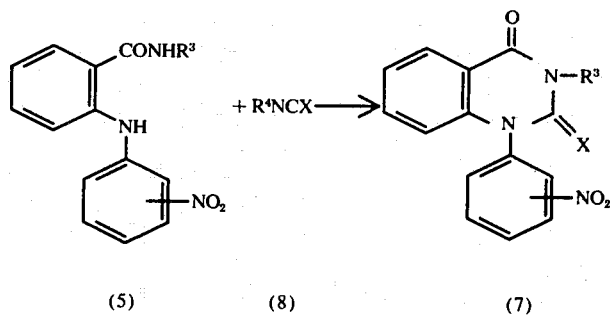

wherein $R^3$ and X have the same meanings as above ; $R^4$ is selected from the group consisting of aryl, cyclohexyl and naphthyl. Examples of compounds of the general formula (8) include phenyl isocyanate and phenyl isothiocyanate.

Reaction scheme [V] :

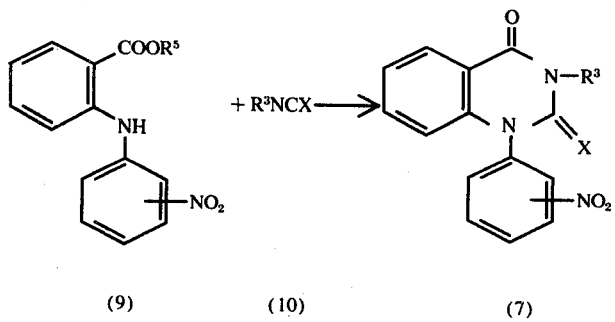

(9)  (10)  (7)

wherein $R^3$ and X have the same meanings as above; $R^5$ is lower alkyl. Examples of compounds of the general formula (10) include methyl isocyanate, ethyl isocyanate, ethyl isothiocyanate and allyl isothiocyanate. The starting materials, 2-nitroanilinobenzamides (5) and 2-nitroanilinobenzoic acid esters (9) can be obtained in high yields by reacting 2-nitroanilinobenzoyl chloride with the corresponding amines or alcohols. The reactions represented by the reaction scheme [III] – [V] are generally carried out in a suitable organic solvent such as tetrahydrofuran, diglyme, benzene, dimethylformamide or alcohol. In the preferred procedure, the reactions should be carried out in the presence of an alkali metal or metallic compound such as metallic sodium, metallic potassium, sodium hydride, sodium amide or sodium alcoholate, an organic base such as pyridine or trialkylamine, or an inorganic base such as alkali hydroxide or alkali carbonate. The employment of the first-mentioned alkali metals or metallic compounds is particularly advantageous in producing the highest yield of the object compounds.

The reaction temperature is not critical. While the reactions proceed smoothly even at room temperature, it is preferable to perform the reactions near the boiling point of the solvent used.

The reaction mixture is concentrated to remove the solvent, and the residue obtained is mixed with water to precipitate a crude product. This product is purified either by recrystallization from an appropriate organic solvent such as methanol or by column chromatography to give pure crystals of the object compounds.

Compounds:

The object compounds of the present invention can be prepared by one of five independent processes as illustrated in the Reaction scheme I–V. Examples of the compounds and the melting points thereof are shown in Table I.

Examples of the compounds obtained by the present invention

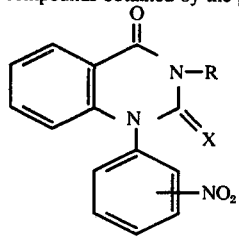

| Compound No. | Position of NO₂ | X | R | Melting point (° C) |
|---|---|---|---|---|
| 1 | meta | O | —H | 285 – 287 |
| 2 | " | " | —CH₃ | 241 – 242 |
| 3 | " | " | —C₂H₅ | 193 – 194 |
| 4 | " | " | —CH₂CH₂CH₃ | 162 – 163 |
| 5 | " | " | —CH(CH₃)₂ | 177 – 178 |
| 6 | " | " | —CH₂CH=CH₂ | 165 – 166 |
| 7 | " | " | —CH₂CH=C(CH₃)₂ | 185 – 186 |
| 8 | " | " | —CH₂C≡CH | 222 – 223 |
| 9 | " | " | —CH₂-cyclopropyl | 163 – 164 |
| 10 | " | " | —CH₂CH₂F | 184 – 185 |
| 11 | " | " | —CH₂CH₂Cl | 170 – 171 |
| 12 | " | " | —CH₂CF₃ | 183 – 184 |
| 13 | " | " | —CH₂CH₂OH | 170 – 172 |
| 14 | " | " | —CH₂CH₂CH₂OH | 143 – 144 |
| 15 | " | " | —CH₂OCH₃ | 165 – 166 |
| 16 | " | " | —CH₂CH₂OC₂H₅ | 161 – 162 |
| 17 | " | " | —CH₂CH₂OCH₂CH₂OH | 136 – 138 |
| 18 | " | " | —CH₂CH₂OCOCH₃ | 140 – 142 |
| 19 | " | " | —CH₂COOC₂H₅ | 211 – 212 |

-continued

Examples of the compounds obtained by the present invention

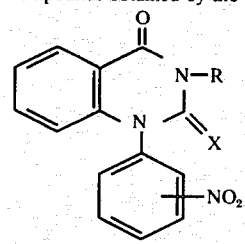

| Compound No. | Position of NO$_2$ | X | R | Melting point (° C) |
|---|---|---|---|---|
| 20 | " | " | —CH$_2$—⌬ | 206 – 207 |
| 21 | para | " | —CH$_3$ | 238 – 239 |
| 22 | " | " | —C$_2$H$_5$ | 175 – 176 |
| 23 | meta | S | —CH$_3$ | 268 – 269 |
| 24 | " | " | —C$_2$H$_5$ | 197 – 198 |
| 25 | " | " | —CH$_2$—◁ | 161 – 163 |
| 26 | " | " | —CH$_2$CF$_3$ | 221 – 222 |

Pharmacological activities

With respect to numerous compounds of the present invention, the acute toxicity was tested to ensure their safety, and further central nervous system depressive, anti-inflammatory and analgetic effects were tested to prove their excellent activities. The results of each test are indicated in Table II. Each test was conducted in the following manner.

1. Acute toxicity

Each test compound suspended in 0.5 % tragacanth-saline solution was administered intraperitoneally or orally to dd-strain male mice (16–24 g). The lethal dose was estimated from the death of animals 72 hours after administration.

2. Anti-inflammtory effect

A group of five Wistar-strain male rats (100–150 g) were orally administered with each test compound suspended in 0.5 % tragacanth-saline solution. After 30 minutes 0.5 %–1.0 % carrageenin suspended in the water for injection was injected subcutaneously to a hind paw. After 3 hours the carrageenin edema was measured by volume and the inhibition percentage was determined with respect to the results for the control animals. The inhibition percentages were shown with the notations as follows:

| less than 15 % : ± | 31–45 % : ++ | more than 61 % : ++++ |
|---|---|---|
| 16–30 % : + | 46–60 % : +++ | |

(3) Analgetic effect

3. Analgetic effect

Each test compound suspended in 0.5% tragacanth-saline solution was orally administered to dd-strain male mice (18–20 g). After one hour 0.6% acetic acid solution was intraperitoneally injected in a volume of 0.1 mr/10 g. The writhing syndrome was observed for 10 minutes from 30 minutes after the injection, and 50% analgetic effective dose (ED$_{50}$) and its 95% confidential limits were calculated by Litchfield-Wilcoxon's method.

4. Central nervous system depressive effect

Each test compound suspended in 0.5% tragacanth-saline solution was injected intraperitoneally to dd-strain male mice (16–24 g). The disappearance of righting reflex was observed under noiseless circumstances. The dose required for the dissappearance of righting reflex is indicated with the following notations:

| more than 1,000 (mg/kg) : — | 100–30 (mg/kg) : ++ |
|---|---|
| 1,000–300 (mg/kg) : ± | 30–10 (mg/kg) : +++ |
| 300–100 (mg/kg) : + | less than 10 (mg/kg) : ++++ |

Table II

Anti-inflammatory, Analgetic and Central Nervous System Depressive Effects, and Acute Toxicity of the Object Compounds of General Formula:

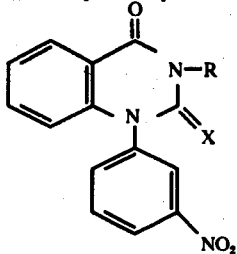

| Standard compounds | anti-inflammatory effect dose(mg/kg) 50 | 10 | analgetic effect ED$_{50}$ (95% C.L.) (mg/kg) | C N S depressive effect | acute toxicity (mg/kg) i.p. |
|---|---|---|---|---|---|
| phenylbutazone | ++ | ± | 290 (113–435) | ± | 300 – 1000 |
| flufenamic acid | + | ± | 180 (131–245) | – | 300 – 1000 |
| aminopyrine | ± | ± | i.p. 56.0 (43.0–73.0) | / | 100 – 300 |
| methaqualone | / | / | / | +++ | 300 – 1000 |
| diazepam | + | ± | / | ++ | 300 – 1000 |

Known analogous compounds

| R$^1$ | R$^2$ | anti-inflammatory effect dose(mg/kg) 50 | 10 | effect ED$_{50}$ (95% C.L.) (mg/kg) | C N S depressive effect | acute toxicity (mg/kg) i.p. | p.o. |
|---|---|---|---|---|---|---|---|
| (3-CF$_3$-phenyl) | —C$_2$H$_5$ | ++ | ± | >100 | – | 456 | >4000 |
| " | —CH$_2$CH$_2$OH | ++ | ± | 35 (28.0–43.0) | ++ | 200 | 970 |

Object compounds

| X | R | anti-inflammatory effect dose(mg/kg) 50 | 10 | analgetic effect ED$_{50}$ (95% C.L.) (mg/kg) | C N S depressive effect | acute toxicity (mg/kg) i.p. | p.o. |
|---|---|---|---|---|---|---|---|
| O | —CH$_3$ | +++ | ++ | 12.5 (6.0–26.3) | + | >1000 | >2000 |
| " | —C$_2$H$_5$ | ++++ | ++++ | 6.0 (2.30–15.6) | ++ | >1000 | >2000 |
| " | —CH$_2$CH$_2$CH$_3$ | + | ± | 51.0 (21.3–122) | – | 1000 | >2000 |
| " | —CH(CH$_3$)$_2$ | +++ | + | 2.9 (1.21–6.95) | ++ | >1000 | >2000 |
| " | —CH$_2$-cyclopropyl | +++ | ++ | 16.5 (6.71–40.6) | + | 1000 | 1000 – 2000 |
| " | —CH$_2$CH=CH$_2$ | ++ | + | >100 | – | >1000 | 2000 |
| " | —CH$_2$C≡CH | ++ | ± | 40.0 (18.2–88.0) | – | >1000 | >2000 |
| " | —CH$_2$CH$_2$Cl | + | / | 5.5 (2.12–14.3) | + | >1000 | >2000 |
| " | —CH$_2$CH$_2$F | +++ | ++++ | 1.48 (0.36–6.02) | ++ | >1000 | >2000 |
| " | —CH$_2$CF$_3$ | ++ | + | 44.0 (14.4–134.2) | – | >1000 | >2000 |
| " | —CH$_2$CH$_2$OH | ++ | / | 2.25 (0.90–5.63) | +++ | 300 – 1000 | 2000 |
| " | —CH$_2$CH$_2$OCOCH$_3$ | + | / | 1.7 (0.60–4.85) | +++ | >1000 | 2000 |
| " | —CH$_2$CH$_2$OC$_2$H$_5$ | + | / | 2.15 | ++ | >1000 | >2000 |

Table II-continued

Anti-inflammatory, Analgetic and Central Nervous System Depressive Effects, and Acute Toxicity of the Object Compounds of General Formula :

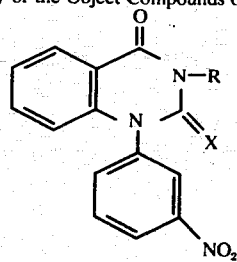

| | | | | | | | |
|---|---|---|---|---|---|---|---|
| " | —CH$_2$CH$_2$OCH$_2$CH$_2$OH | + | / | (0.73–6.30) 3.7 | ++ | 1000 | 2000 |
| S | —CH$_3$ | + | ± | (1.48–9.25) >100 | — | >1000 | / |
| " | —C$_2$H$_5$ | +++ | ++ | 3.4 | ± | >1000 | / |
| " | —CH$_2$CF$_3$ | ± | / | (1.48–7.82) >100 | — | >1000 | >2000 |

The present invention is illustrated hereinafter, but not limited to the Examples.

EXAMPLE 1

To a solution of 2.8 g of 1-(m-nitrophenyl)quinazoline-2,4(1H, 3H)-dione and 30 ml of dimethylformamide was added 0.5 g of approximately 55% sodium hydride, and the solution was stirred for 30 minutes. To this was further added 4.7 g of ethyl iodide and stirring was further continued for 1.5 hours at room temperature. After the reaction was complete, the solvent was distilled off from the mixture under reduced pressure. To the residue obtained was added water to precipitate a crude product, which was then recrystallized from methanol to give 2.7 g of 1-(m-nitrophenyl)-3-ethyl-quinazoline-2,4 (1H, 3H)-dione as light brown prisms, melting at 193°–194° C.

Analysis-Calculated for C$_{16}$H$_{13}$N$_3$O$_4$ : C, 61.73 ; H, 4.21 ; N, 13.50. Found : C, 61.76 ; H, 4.11 ; N, 13.46.

EXAMPLE 2

To a solution of 2.8 g of 1-(m-nitrophenyl)quinazoline-2,4(1H, 3H)-dione and 30 ml of dimethylformamide was added 0.6 g of approximately 55% sodium hydride, and the solution was stirred for 30 minutes. Then the solution was heated up to 60° C, and to this was further added dropwise 6 g of ethyl p-toluenesulfonate dissolved in 15 ml of dimethylformamide, and the whole was reacted for 1.5 hours at 60° C. After the reaction was finished, the solvent was evaporated from the mixture under reduced pressure, and to the residue obtained was added water to precipitate a crude product. Recrystallization of this product from methanol gave 2.4 g of 1-(m-nitrophenyl) -3-ethylquinazoline-2,4(1H, 3H)-dione as light brown prisms, melting at 193°–194° C.

EXAMPLE 3

To a solution of 2.8 g of 1-(m-nitrophenyl)quinazoline-2,4(1H, 3H)-dione and 30 ml of dimethylformamide was added 0.6 g of approximately 55% sodium hydride and the solution was stirred for 30 minutes at room temperature. To this was further added 3.6 g of allyl bromide, and the mixture was reacted for 2 hours at room temperature. Then, the solvent was distilled off from the resulting mixture under reduced pressure to leave a residue, to which was added water to precipitate a crude product. This product was recrystallized from methanol to yield 2.9 g of 1-(m-nitrophenyl)-3-allylquinazoline-2,4(1H, 3H)-dione as light brown needles, melting at 165°–166° C.

Analysis-Calculated for C$_{17}$H$_{13}$N$_3$O$_4$: C, 63.15 ; H, 4.05 ; N, 13.00. Found : C, 63.21 ; H, 4.12 ; N, 12.93.

EXAMPLE 4

To a solution of 2.8 g of 1-(m-nitrophenyl)quinazoline-2,4(1H, 3H)-dione and 30 ml of dimethylformamide was added 0.6 g of approximately 55% sodium hydride, and the solution was stirred for 30 minutes at room temperature. To this was added 2.3 g of methyl fluorosulfate, and the whole was reacted for one hour at room temperature. After the reaction was complete, the solvent was distilled off from the reaction mixture under reduced pressure. To the residue obtained was added water to precipitate a crude product. Recrystallization of this product from methanol gave 2.7 g of 1-(m-nitrophenyl)-3-methylquinazoline-2,4(1H, 3H)-dione as colorless needles, melting at 241°–242° C.

Analysis-Calculated for C$_{15}$H$_{11}$N$_3$O$_4$: C, 60.60 ; H, 3.73 ; N, 14.14. Found : C, 60.80 ; H, 3.67 ; N, 14.16.

EXAMPLE 5

To a solution of 2.8 g of 1-(m-nitrophenyl)quinazoline-2,4(1H, 3H)-dione and 30 ml of dimethylformamide was added 0.6 g of approximately 55% sodium hydride, and the solution was stirred for 20 minutes at room temperature. To this was added 2.2 g of dimethyl sulfite and stirring was further continued for 4 hours at room temperature. After the reaction was complete, the solvent was removed from the reaction mixture by distillation under reduced pressure. The residue thus obtained was mixed with water to precipitate a crude product. This product was recrystallized from methanol to afford 2.8 g of 1-(m-nitrophenyl)-3-methylquinazoline-2,4(1H, 3H)-dione as colorless needles, melting at 242°–243° C.

EXAMPLE 6

To a solution of 2.8 g of 1-(m-nitrophenyl)quinazoline-2,4(1H, 3H)-dione and 20 ml of dimethylformamide was added 4.2 g of trimethyl phosphate and the whole was refluxed for 5 hours. After the reaction was complete, the solvent was distilled off from the reaction mixture under reduced pressure. To the residue thus obtained was added water to precipitate a crude product. This product was recrystallized from methanol to yield 2.4 g of 1-(m-nitrophenyl)-3-methylquinazoline-2,4(1H, 3H)-dione as colorless needles, melting at 241°–242° C.

EXAMPLE 7

To a solution of 2.8 g of 1-(m-nitrophenyl)quinazoline-2,4(1H, 3H)-dione and 30 ml of dimethylformamide was added 1.4 g of sodium ethoxide, and the whole was stirred for 30 minutes at room temperature. To this was further added 4.1 g of cyclopropylmethyl bromide, and the mixture was reacted for 2 hours at room temperature. Then, the solvent was distilled off from the resulting mixture under reduced pressure to leave a residue, to which was added water to precipitate a crude product. Recrystallization of this product from methanol gave 3.1 g of 1-(m-nitrophenyl)-3-cyclopropylmethyl-quinazoline-2,4(1H, 3H)-dione as colorless needles, melting, at 163°–164° C.

Analysis-Calculated for $C_{18}H_{15}N_3O_4$: C, 64.09 ; H, 4.48 ; N, 12.46. Found : C, 63.86 ; H, 4.34 ; N, 12.58.

EXAMPLE 8

A mixture of 2.8 g of 1-(m-nitrophenyl)quinazoline-2,4(1H, 3H)-dione, 40 ml of dry tetrahydrofuran and 4.4 g of N,N-dimethylformamide diethyl acetal was refluxed for 6 hours. After the reaction was complete, the solvent was distilled off from the reaction mixture under reduced pressure. To the residue obtained was added water to precipitate a crude product, which was then recrystallized from methanol to produce 2.8 g of 1-(m-nitrophenyl)-3-ethylquinazoline-2,4(1H, 3H)-dione as colorless prisms, melting at 193°–194° C.

EXAMPLE 9

To a solution of 2.9 g of 2-(m-nitroanilino)-N-ethylbenzamide and 25 ml of tetrahydrofuran was added 1.0 g of 50% sodium hydride, and stirring was performed for 30 minutes at room temperature. To this was added dropwise under cooling 5.4 g of ethyl chlorocarbonate, and the mixture was allowed to stand for one hour at room temperature and then refluxed for 10 hours. After the reaction was complete, the solvent was evaporated from the reaction mixture under reduced pressure, and to the residue obtained was added water to prepicpitate a crude product. This product was recrystallized from methanol to give 2.5 g of 1-(m-nitrophenyl)-3-ethylquinazoline-2,4(1H, 3H)-dione as colorless prisms, melting at 193°–194° C.

EXAMPLE 10

To a solution of 3.0 g of 2-(m-nitroanilino)-N-allylbenzamide and 25 ml of tetrahydrofuran was added 1.1 g of 50% sodium hydride, and the whole was stirred for 30 minutes at room temperature. To this was added dropwise under cooling 16 g of 30% phosgene-toluene solution, and the mixture was stirred for one hour at room temperature and then refluxed for 2 hours. After the reaction was finished, the solvent was distilled off from the resulting mixture, and to the residue obtained was added water to precipitate a crude product. This product was recrystallized from methanol to yield 2.8 g of 1-(m-nitrophenyl)-3-allylquinazoline-2,4(1H, 3H)-dione as colorless needles, melting at 164°–166° C.

EXAMPLE 11

To a solution of 2.7 g of 2-(m-nitroanilino)-N-methylbenzamide and 25 ml of tetrahydrofuran were added 1.0 g of 50% sodium hydride and 5.9 g of diethyl carbonate, and the whole was refluxed for 12 hours. After the reaction was complete, the solvent was removed from the reaction mixture under reduced pressure. To the residue obtained was added water to precipitate a crude product. This product was recrystallized from methanol to yield 2.4 g of 1-(m-nitrophenyl)-3-methylquinazoline-2,4(1H, 3H)-dione as colorless needles, melting at 241°–242° C.

EXAMPLE 12

To a solution of 3.0 g of 2-(m-nitroanilino)-N-propylbenzamide and 50 ml of tetrahydrofuran were added 1.1 g of 50% sodium hydride and 4.9 g of 1,1'-carbonyldiimidazole. The mixture was stirred for one hour at room temperature and then refluxed for 5 hours. After the reaction was finished, the solvent was distilled off from the resulting mixture under reduced pressure, and to the residue obtained was added water to yield a precipitate. This product was recrystallized from methanol to yield 2.6 g of 1-(m-nitrophenyl)-3-propylquinazoline-2,4(1H, 3H)-dione as colorless prisms, melting at 162°–163° C.

Analysis-Calculated for $C_{17}H_{15}N_3O_4$: C, 62.76 ; H, 4.65 ; N, 12.92. Found : C, 62.68 ; H, 4.62 ; N, 12.87.

EXAMPLE 13

To a solution of 3.0 g of 2-(m-nitroaniline)-N-cyclopropylmethylbenzamide and 25 ml of dry tetrahydrofuran was added 1.0 g of approximately 55 % sodium hydride, and stirring was then performed for 30 minutes at room temperature. To this was added dropwise 4.2 g of 1-ethoxycarbonylimidazole and the mixture was refluxed for 3 hours. After the reaction was complete, the solvent was evaporated from the resulting mixture under reduced pressure, and to the residue obtained was added water to yield a precipitate. This product was recrystallized from methanol to yield 2.6 g of 1-(m-nitrophenyl)- 3-cyclopropylmethylquinazoline-2,4(1H, 3H)-dione as colorless needles, melting at 163°–164° C.

Analysis-Calculated for $C_{18}H_{15}N_3O_4$: C, 64.09 ; H, 4.49 ; N, 12.46. Found : C, 63.86 ; H, 4.52 ; N, 12.57.

EXAMPLE 14

To a solution of 3.0 g of 2-(m-nitroanilino)-N-propargylbenzamide and 25 ml of dry tetrahydrofuran was added 1.0 g of approximately 55 % sodium hydride, and the solution was stirred for 30 minutes at room temperature. To this was added dropwise 2.1 g of 1-trichloroacetylimidazole and the mixture was refluxed for one hour. After the reaction was complete, the solvent was distilled off from the resulting mixture under reduced pressure. To the residue thus obtained was added water to yield a crude product. This product was recrystallized from methanol to yield 2.8 g of 1-(m-nitrophenyl) -3-propargylquinazoline-2,4(1H, 3H)-dione as colorless needles, melting at 222°–223° C.

Analysis-Calculated for $C_{17}H_{11}N_3O_4$: C, 63.55 ; H, 3.45 ; N, 13.08. Found : C, 63.48 ; H, 3.51 ; N, 13.11.

EXAMPLE 15

To a solution of 3.4 g of 2-(m-nitroanilino)-N-(2,2,2-trifluoroethyl) benzamide and 25 ml of dry tetrahydrofuran was added 0.5 g of approximately 55 % sodium hydride, and stirring was continued for one hour at room temperature. To this was added dropwise under cooling 5.5 g of trichloroacetyl chloride and the mixture was allowed to stand for one hour at room temperature, and then refluxed for 5 hours. After the reaction was complete, the solvent was distilled off from the resulting mixture under reduced pressure. To the residue was added water to precipitate a crude product. This product was recrystallized from ethanol to give 3.2 g of 1-(m-nitrophenyl)-3-(2,2,2-trifluoroethyl) quinazoline-2,4(1H, 3H)-dione as pale yellow prisms, melting at 182°–184° C.

Analysis-Calculated for $C_{16}H_{10}F_3N_3O_4$: C, 52.61; H, 2.76; N, 11.51. Found: C, 52.75; H, 2.89; N, 11.45.

EXAMPLE 16

To a solution of 3.5 g of 2-(m-nitroanilino)-N-benzylbenzamide and 30 ml of dry tetrahydrofuran was added 1.0 g of about 55 % sodium hydride, and stirring was performed for 30 minutes at room temperature. To this was added dropwise a solution of 4.9 g of 1-[N-(m-chlorophenyl)carbamoyl]imidazole and 30 ml of dry tetrahydrofuran. The mixture was allowed to stand for 30 minutes at room temperature and then refluxed for 2 hours. After the reaction was complete, the resulting mixture was filtered. The filtrate was concentrated under reduced pressure to leave a residue, to which was added water to precipitate a crude product. Recrystallization of this product from methanol gave 2.0 g of 1-(m-nitrophenyl)-3-benzylquinazoline-2,4(1H, 3H)-dione as colorless prisms, melting at 206°–207° C.

Analysis-Calculated for $C_{21}H_{15}N_3O_4$: C, 67.55; H, 4.05; N, 11.26. Found: C, 67.45; H, 4.10; N, 11.32.

EXAMPLE 17

3.3 g of 2-(m-nitroanilino)-N-(2-ethoxyethyl)benzamide was dissolved in 30 ml of dry tetrahydrofuran, and to the solution was added 1.0 g of approximately 50 % sodium hydride. After stirring the mixture for 30 minutes, 3.2 g of N,N-dimethylcarbamoyl chloride was further added dropwise under cooling, and the whole was refluxed for 4 hours. After the reaction was complete, the solvent was evaporated from the resulting mixture under reduced pressure. To the residue thus obtained was added water to yield a crude product. This product was recrystallized from ethanol to give 3.1 g of 1-(m-nitrophenyl)-3-(2-ethoxyethyl)quinazoline-2,4(1H, 3H)-dione as pale yellow prisms, melting at 161°–162° C.

Analysis-Calculated for $C_{18}H_{17}N_3O_5$: C, 60.84; H, 4.82; N, 11.83. Found: C, 60.67; H, 4.72; N, 11.78.

EXAMPLE 18

3.0 g of 2-(m-nitroanilino)-N-allylbenzamide was dissolved in 20 ml of tetrahydrofuran. To the solution was added 1.0 g of approximately 50 % sodium hydride and stirring was performed for 30 minutes. To this was added dropwise under cooling 4.6 g of m-chlorophenyl isocyanate, and the mixture was stirred for one hour, and then refluxed for 5 hours. After the reaction was complete, the solvent was distilled off from the resulting mixture. The residue thus obtained was recrystallized from methanol to give 2.3 g of 1-(m-nitrophenyl)-3-allylquinazoline-2,4(1H, 3H)-dione as colorless needles, melting at 165°–166° C.

EXAMPLE 19

To a solution of 2.6 g of 2-(m-nitroanilino)-N-methylbenzamide and 20 ml of tetrahydrofuran was added 0.86 g of sodium amide, and the whole was stirred for 30 minutes at room temperature. To this was added dropwise under cooling 3.6 g of phenyl isocyanate, and the mixture was stirred for one hour at room temperature, and then refluxed for 4 hours. After the reaction was finished, the solvent was distilled off from the resulting mixture. The residue thus obtained was recrystallized from methanol to give 2.2 g of 1-(m-nitrophenyl)-3-methylquinazoline-2,4(1H, 3H)-dione as colorless needles, melting at 241°–242° C.

EXAMPLE 20

To a solution of 2.9 g of 2-(m-nitroanilino)-N-ethylbenzamide and 20 ml of tetrahydrofuran was added 1.0 g of approximately 50 % sodium hydride, and the whole was stirred for 30 minutes at room temperature. To this was added dropwise under cooling 4.1 g of phenyl isothiocyanate, and the mixture was stirred for one hour at room temperature, and then refluxed for 4 hours. After the reaction was complete, the solvent was distilled off from the resulting mixture. The residue thus obtained was extracted with chlorform and the chloroform solution was chromatographed on a column of alumina, and then eluted with chloroform. The solvent was distilled off from the eluate under reduced pressure, and the residue was recrystallized from methanol to give 1.0 g of 1-(m-nitrophenyl)-3-ethyl-2-thio-4-oxo-1,2,3,4-tetrahydroquinazoline as colorless prisms, melting at 196°–198° C.

EXAMPLE 21

To a solution of 2.9 g of 2-(m-nitroanilino)benzoic acid methyl ester and 20ml of dry dimethylformamide was added 0.43 g of sodium amide, and the whole was stirred for 30 minutes. To this was added dropwise under cooling 2.6 g of propyl isocyanate. This mixture was allowed to stand for one hour at room temperature and for additional one hour at 60° C, and then reacted for 4 hours at 120° C. The solvent was distilled off from the mixture under reduced pressure. To the residue obtained was added water to precipitate a crude product. This product was recrystallized from methanol to produce 2.4 g of 1-(m-nitrophenyl)-3-propylquinazoline-2,4(1H, 3H)-dione as colorless needles, melting at 162°–163° C.

EXAMPLE 22

3.0 g of 2-(m-nitroanilino)benzoic acid ethyl ester was dissolved in 20 ml of tetrahydrofuran. To the solution was added 0.53 g of approximately 50 % sodium hydride, and the whole was stirred for 30 minutes at room temperature. Further, to this was added dropwise under ice-cooling 2.5 g of ethyl isothiocyanate. The mixture was allowed to stand for 30 minutes under cooling and warmed gradually to 70° C, at which temperature it was reacted for 5 hours. After the reaction was complete, the solvent was removed from the resulting mixture by distillation. The residue obtained was recrystallized from methanol to produce 1-(m-nitrophenyl)-3-ethyl-2-thio-4-oxo-1,2,3,4-tetrahydroquinazoline as pale yellow prisms, melting at 197°–198° C.

Analysis-Calculated for $C_{16}H_{13}N_3O_3S$: C, 58.70; H, 4.00; N, 12.84. Found: C, 58.32; H, 3.92; N, 12.91.

What is claimed is:

1. A compound of the general formula:

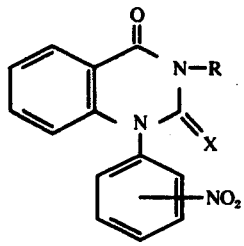

wherein R is selected from the group consisting of hydrogen, lower alkyl groups having from one to 6 carbon atoms, lower alkenyl groups having from 3 to 5 carbon atoms, propargyl, cyclopropylmethyl, haloethyl, trihaloethyl, acetoxyethyl, alkoxyalkyl groups having from 2 to 4 carbon atoms, lower hydroxyalkyl groups having from 2 to 3 carbon atoms, hydroxyethoxyethyl, ethoxycarbonylmethyl and benzyl; X is selected from the group consisting of O and S.

2. A compound in accordance with claim 1 of the formula :

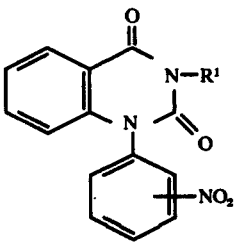

wherein $R^1$ is selected from the group consisting of hydrogen, lower alkyl groups having from one to 6 carbon atoms, lower alkenyl groups having from 3 to 5 carbon atoms, propargyl, cyclopropylmethyl, haloethyl, trihaloethyl, acetoxyethyl, alkoxyalkyl groups having from 2 to 4 carbon atoms, lower hydroxyalkyl groups having from 2 to 3 carbon atoms, hydroxyethoxyethyl, ethoxycarbonylmethyl and benzyl.

3. A compound in accordance with claim 1 of the formula :

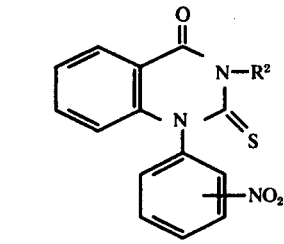

wherein $R^2$ is selected from the group consisting of lower alkyl groups having from one to 6 carbon atoms, trihaloethyl and cyclopropylmethyl.

4. 1-(m-nitrophenyl )-3-methylquinazoline-2,4(1H, 3H)-dione in accordance with claim 1.

5. 1-(m-nitrophenyl)-3-ethylquinazoline-2,4(1H, 3H)-dione in accordance with claim 1.

6. 1-(m-nitrophenyl)-3-isopropylquinazoline-2,4(1H, 3H)-dione in accordance with claim 1.

7. 1-(m-nitrophenyl)-3-cyclopropylmmethylquinazoline-2,4(1H, 3H)-dione in accordance with claim 1.

8. 1-(m-nitrophenyl)-3-(2-chloroethyl)quinazoline-2,4(1H, 3H)-dione in accordance with claim 1.

9. 1-(m-nitrophenyl)-3-(2-fluoroethyl)quinazoline-2,4(1H, 3H)-dione in accordance with claim 1.

10. 1-(m-nitrophenyl)-3-(2-hydroxyethyl)quinazoline-2,4(1H, 3H)-dione in accordance with claim 1.

11. 1-(m-nitrophenyl)-3-(2-acetoxyethyl)quinazoline-2,4(1H, 3H)-dione in accordance with claim 1.

12. 1-(m-nitrophenyl)-3-(2-ethoxethyl) quinazoline-2,4(1H, 3H)-dione in accordance with claim 1.

13. 1-(m-nitrophenyl)-3-(2-(hydroxyethoxy)ethyl) quinazoline-2,3,(1H,3H)-dione in accordance with claim 1.

14. 1-(m-nitrophenyl)-3-ethyl-2-thio-4-oxo-1,2,3,4-tetrahydroquinazoline in accordance with claim 1.

* * * * *